United States Patent
Traneus

(10) Patent No.: US 12,147,734 B2
(45) Date of Patent: Nov. 19, 2024

(54) STATIC DEVICE FOR USE IN RADIOTHERAPY TREATMENT AND DESIGN METHOD FOR SUCH A DEVICE

(71) Applicant: RaySearch Laboratories AB (Publ), Stockholm (SE)

(72) Inventor: Erik Traneus, Uppsala (SE)

(73) Assignee: Raysearch Laboratories AB (publ), Stockholm (SE)

(*) Notice: Subject to any disclaimer, the term of this patent is extended or adjusted under 35 U.S.C. 154(b) by 0 days.

(21) Appl. No.: 18/040,981

(22) PCT Filed: Jul. 26, 2021

(86) PCT No.: PCT/EP2021/070785
§ 371 (c)(1),
(2) Date: Feb. 8, 2023

(87) PCT Pub. No.: WO2022/037901
PCT Pub. Date: Feb. 24, 2022

(65) Prior Publication Data
US 2023/0214542 A1 Jul. 6, 2023

(30) Foreign Application Priority Data
Aug. 21, 2020 (EP) .................... 20192106

(51) Int. Cl.
G06F 30/10 (2020.01)
A61N 5/10 (2006.01)
(Continued)

(52) U.S. Cl.
CPC ........... G06F 30/10 (2020.01); A61N 5/1043 (2013.01); A61N 5/1071 (2013.01);
(Continued)

(58) Field of Classification Search
CPC ..... G06F 30/10; G06F 2111/16; A61N 5/103; A61N 5/1043; A61N 5/1071; A61N 5/1077; A61N 2005/1087; G21K 1/02
See application file for complete search history.

(56) References Cited

U.S. PATENT DOCUMENTS 7,268,358 B2 * 9/2007 Ma ........................... G21K 5/04
  250/492.23
8,986,186 B2 * 3/2015 Zhang ..................... A61N 5/103
  600/1
(Continued)

FOREIGN PATENT DOCUMENTS

| CN | 109310881 A | 2/2019 |
| CN | 110691627 A | 1/2020 |

OTHER PUBLICATIONS

Kramer, M., et al. "Treatment planning for heavy-ion radiotherapy: physical beam model and dose optimization" Phys. Med. Biol., vol. 45, pp. 3299-3317 (2000) (Year: 2000).*

(Continued)

*Primary Examiner* — Jay Hann
(74) *Attorney, Agent, or Firm* — Noréns Patentbyrå AB

(57) ABSTRACT

A compensating device for use in ion-based radiotherapy may comprise a disk with a number of protrusions may be placed in a radiation beam to affect the ions in the beam in different ways to create an irradiation field from a broad beam. This is particularly useful in FLASH therapy because of the limited time available or modulating the beam. A method of designing such a compensating device is proposed, comprising the steps of obtaining characteristics of an actual treatment plan comprising at least one beam, determining at least one parameter characteristic of the desired energy modulation of the actual plan by performing a dose calculation of the initial plan and, based on the at least one parameter, computing a shape for each of the plurality (Continued)

of elongated elements to modulate the dose of the delivery beam to mimic the dose of the initial plan per beam.

13 Claims, 2 Drawing Sheets

(51) Int. Cl.
  *G06F 111/16* (2020.01)
  *G21K 1/02* (2006.01)
(52) U.S. Cl.
  CPC .......... *A61N 2005/1087* (2013.01); *A61N 2005/1096* (2013.01); *G06F 2111/16* (2020.01); *G21K 1/02* (2013.01)

(56) References Cited

U.S. PATENT DOCUMENTS

| | | | |
|---|---|---|---|
| 9,119,962 B2* | 9/2015 | Bert | A61N 5/1043 |
| 10,315,047 B2* | 6/2019 | Glimelius | A61N 5/1031 |
| 10,850,119 B2* | 12/2020 | Meltsner | A61N 5/103 |
| 11,554,271 B2* | 1/2023 | Smith | G16H 50/20 |
| 2012/0157746 A1 | 6/2012 | Meltsner et al. | |
| 2019/0046813 A1* | 2/2019 | Zhou | A61N 5/10 |

OTHER PUBLICATIONS

Kramer, M. & Scholz, M. "Treatment planning for heavy-ion radiotherapy: calculation and optimization of biologically effective dose" Phys. Med. Biol., vol. 45, pp. 3319-3330 (2000) (Year: 2000).*

Sakae, T., et al. "Multi-layer energy filter for realizing conformal irradiation in charged particle therapy" Med. Phys., vol. 27, No. 2, pp. 368-373 (2000) (Year: 2000).*

Akulinichev, S., et al. "Possible improvement of proton energy filter for radiotherapy" Nuclear Inst. & Methods in Physics Research, vol. A 997, 164296 (Jun. 2020) (Year: 2020).*

Yuri Simeonov et al, "3D range-modulator for scanned particle therapy: development, Monte Carlo simulations and experimental evaluation", Aug. 11, 2017 (Aug. 11, 2017), vol. 62, No. 17, p. 7075-7096,XP020319397, DOI: 10.1088/1361-6560/AA81F4 external link, ISSN:0031-9155.

International Search Report & Written Opinion, European Patent Office, Oct. 11, 2021, Rijswijk, Netherlands.

Office Action dated May 22, 2023 in corresponding Chinese patent application No. 202180039559.3, China.

Office Action dated Mar. 28, 2024 in coresponding Chinese application No. 202180039559.3, Chinese Patent Office, China.

* cited by examiner

STATIC DEVICE FOR USE IN RADIOTHERAPY TREATMENT AND DESIGN METHOD FOR SUCH A DEVICE

TECHNICAL FIELD

The present invention relates to a passive device for use in radiotherapy treatment and to a method of designing such a device.

BACKGROUND

In ion-based radiotherapy treatment, a patient is irradiated with a beam of protons or some other type of ion. Ion-based treatment is advantageous because the volume in which each ion deposits its energy can be controlled with high precision by controlling the ion's energy and direction. A common way of achieving a homogeneous or in-homogeneous irradiation field is to use pencil beam scanning in which many small beams of different directions and energy levels are directed at different points within the target. The term pencil beam scanning includes a number of different scanning methods, such as spot scanning, or line scanning or raster scanning.

In some cases, however, it is desirable to shape and modulate the field using a static broad beam with a single energy in combination with different types of active or passive devices to shape the field.

It is known in ion-based radiotherapy to use passive devices such as compensators to control the maximum range of the ions by providing an element of varying thickness made from a material that will attenuate the energy of the ions, thus shortening their path in dependence of the thickness of the compensator.

The point in which an ion deposits the main part of its energy is known as the Bragg peak, and is well defined near the end of the ion's trajectory. In addition to affecting the position of the Bragg peaks by means of compensators, devices for spreading the Bragg peaks in the depth direction to achieve homogeneous dose coverage over the target volume are known. To achieve this, a rotating disk having areas of different thicknesses is commonly used and rotating at approximately 30 rounds per second has been used. Other devices include ripple filters, also called ridge filters, which are semi-transparent devices comprising a disk with a regular pattern of ridges that will modulate the beams to broaden Bragg peaks in the depth direction.

In recent years, FLASH therapy has become of interest as it promises efficient treatment in shorter and fewer fractions, with additional benefits therefore saving hospital resources and also more efficient from the point of view of the patient. In FLASH therapy, treatment irradiation is given in very short pulses of very high dose rates, typically a fraction of a second at a dose rate of 40 Gy/s or more. The time aspect is critical for achieving the advantages associated with FLASH treatment. With such short times, treatments with scanning beams must be given at one single energy level, since every change in the energy level takes on the order of magnitude of one second. Traditional pencil beam scanning methods therefore do not work. Further, the rotating disk used in conventional passive therapy to create the spread-out Bragg peak also will not be feasible.

Simeonov et al. 3D range-modulator for scanned particle therapy: development, Monte Carlo simulations and experimental evaluation; 2017 Phys. Med. Biol. 62 7075, propose a static element comprising a disk of varying thickness effectively functioning as a compensator and with a number of thin pins of with a well-defined shape and different lengths arranged on a surface of the disk to modulate the necessary shift of the Bragg peak. This element combines the function of a compensator and energy filter in such a way as to allow PBS plans to be delivered with only a single energy layer per beam to reduce delivery time. The element is designed by means of ray tracing combined with the concept of radiological path length, based on the patient's geometry and the desired dose in the target. In practice this involves following a number of lines of sight through the patient, registering the depths where the line intersects with the proximal and distal surface of the target. The disk part is designed with varying thickness to serve as a compensator adapted to the distal surface of the target and the proximal-distal distance is used to calculate the lengths and shape of the pins in such a way that the field will cover the whole target. This method enables a static device that is able to create a homogeneous dose distribution conformed to both the distal and the proximal edge of the target. The device may be manufactured by 3D printing.

There is a desire to be able to create a more complex dose distribution, for example, to enable co-optimization of overlapping fields.

SUMMARY OF THE INVENTION

The disclosure relates to a method of designing a compensating device for use in ion-based radiotherapy treatment delivery, said device including a substantially disk-shaped structure including on one side of the disk a plurality of elongate elements, said method comprising the steps of
obtaining a pencil beam scanning initial treatment plan
obtaining characteristics of an actual treatment plan comprising at least one beam to be used for treating the patient.
determining at least one parameter characteristic of the desired energy modulation of the actual plan by performing a dose calculation of the initial plan
based on the at least one parameter, computing a shape for each of the plurality of elongate elements to modulate the dose of the delivery beam to mimic the dose of the initial plan per beam.

The method may include calculating the dose of the actual plan and scoring the quantities scored for pixels placed on a virtual grid projected upstream of the patient in the beam trajectory of the at least one beam. The virtual grid enables the definition of a pixel grid The step of computing a shape also includes selecting a material for the elongate body or bodies. Alternatively, the material may have been selected beforehand. The combination of shape and material properties determines how the beam is affected by the elongate element.

In some embodiments, the at least one parameter for determining the height and shape of the elongate bodies includes one or more of the following:
energy layer index spectrum of the initial plan,
the energy spectrum of the initial plan
water equivalent depth spectrum at the primary proton trackends of the initial plan.

The actual plan may include a homogeneous radiation field. The actual plan may be used as a final plan for delivery to the patient, either as it is or after additional optimization steps after the compensating device has been designed. In the latter case, the method comprises the step of reoptimizing the actual plan taking the compensating device into account in the reoptimization, to produce the final plan to be used in delivery to the patient.

To prepare for production of the resulting compensating device, the method may comprise the step of obtaining element shape data indicating the shape of each elongate element, based on the actual plan and using the element shape data to generate a file comprising instructions for the design of the compensating device. The file may be used to control a manufacturing process, performed, for example by a 3D printer.

The actual or final treatment plan may be a pencil beam scanning plan or a broad beam plan i.e. a double scattering plan or a single scattering plan or a wobbling plan, with a single energy, that is, without a spread-out Bragg peak. As mentioned above, the term pencil beam scanning covers a number of different scanning methods, including spot scanning, line scanning or raster scanning.

The disclosure also relates to a method of manufacturing a compensating device for use in ion-based radiotherapy treatment delivery, comprising performing the method according to any one of the preceding claims, using the shape data resulting from the plan to generate a file comprising instructions for the design of the compensating device.

The disclosure also relates to a computer program product comprising computer-readable code means which, when run in a computer will cause the computer to perform the method according to any one of the embodiments discussed above. The computer product may comprise a non-transitory storage holding the code means.

The disclosure also relates to a computer system comprising a program memory and a processing means arranged to execute a program found in the program memory, said program memory comprising a computer program product according to the above.

The compensation device is suitable for use with different types of ion-based radiotherapy treatment. It is well suited for use in FLASH therapy since it is a passive component that works without any moving parts during the treatment; however, it may be used also for conventional therapy. It will enable a reduction in the number of energy levels used during treatment, and even enable full target coverage using only one energy level.

The design method herein described allows complex criteria to be considered when designing the compensator element, since any desired criterion may be expressed as part of an initial optimization problem, including variable Relative Biological Effectiveness (RBE) dose optimization, Linear Energy Transfer (LET) objectives and beam specific objective functions. Therefore, co-optimization of overlapping fields is enabled. Robust optimization with respect to uncertainties in factors such as position and density may also be applied, which will result in a plan that will work more reliably in different scenarios.

BRIEF DESCRIPTION OF DRAWINGS

The invention will be described in more detail in the following, by way of examples and with reference to the appended drawings.

DETAILED DESCRIPTION OF EMBODIMENTS

Figure 1:
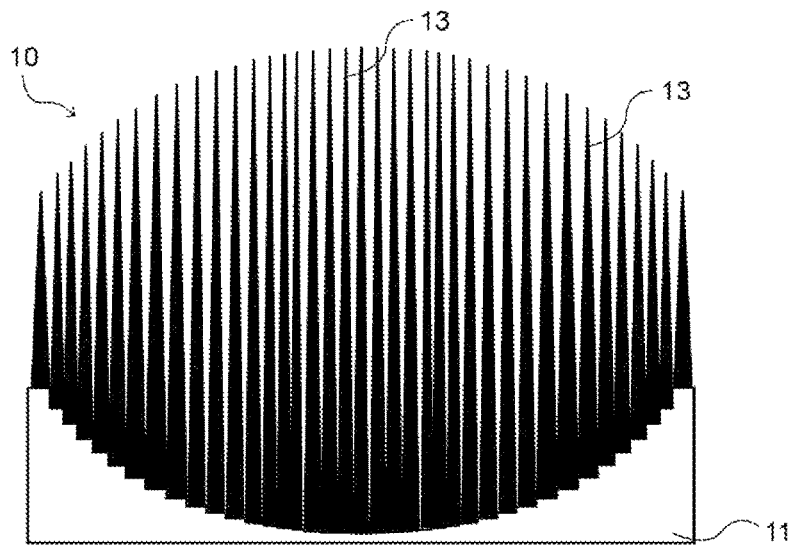
FIG. 1 illustrates an example of a device as disclosed in this description

FIG. 1 shows an example of a passive modulation device 10 according to embodiments of the invention. The device comprises a compensator element 11 which is essentially a disk having varying thickness across its area. The thickness is designed to cause an incoming radiation field to conform to the distal end of the target. On the disk a number of protrusions in the form of spike-shaped structures 13 are arranged, typically of the same material as the compensator element. The protrusions 13 are typically placed in a grid pattern on the disk, each occupying an area of, for example, $1.5 \times 1.5$ mm$^2$ of the disk. The protrusions 13 have different heights and shapes, selected in such a way that a beam passing through the device will be modulated to have Bragg peaks covering the whole of a target in a desired way. Of course, the size, shape and thickness of the compensator element, the arrangement of the protrusions on the compensator element and their size and heights, should be selected to conform to the target.

Figure 2A:
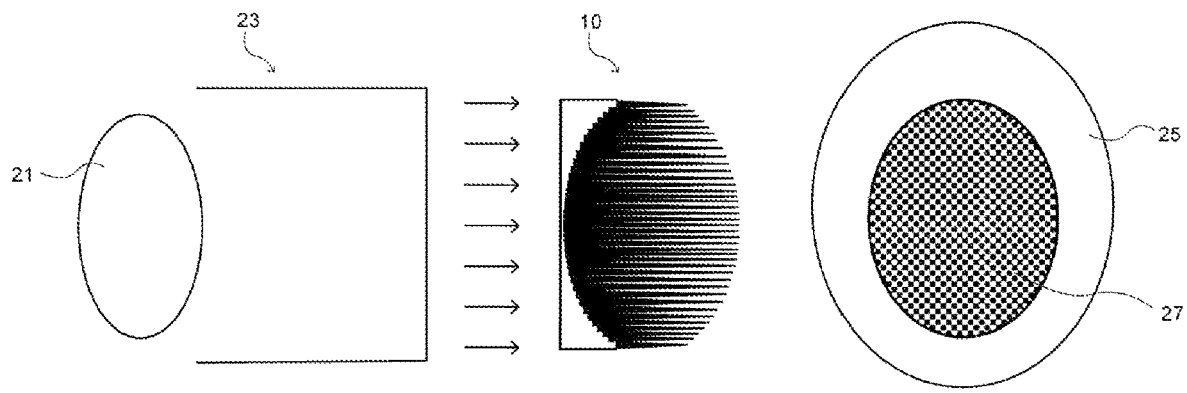
FIG. 2a illustrates how the device of FIG. 1 may be applied in radiation therapy.

FIG. 2a shows the device of FIG. 1 inserted between a source 21 of radiation emitting a homogeneous radiation field 23, and a patient 25, shown simplified as an elliptic form and comprising a target 27. The radiation field is modulated by the device 10 in such a way that the energy spectrum of the radiation after passing through the device will create a field that conforms to the shape of the target. In FIG. 2a, the target is shown to have a simple nearly circular form but according to the invention, more complex shapes can be treated as well.

Figure 2B:
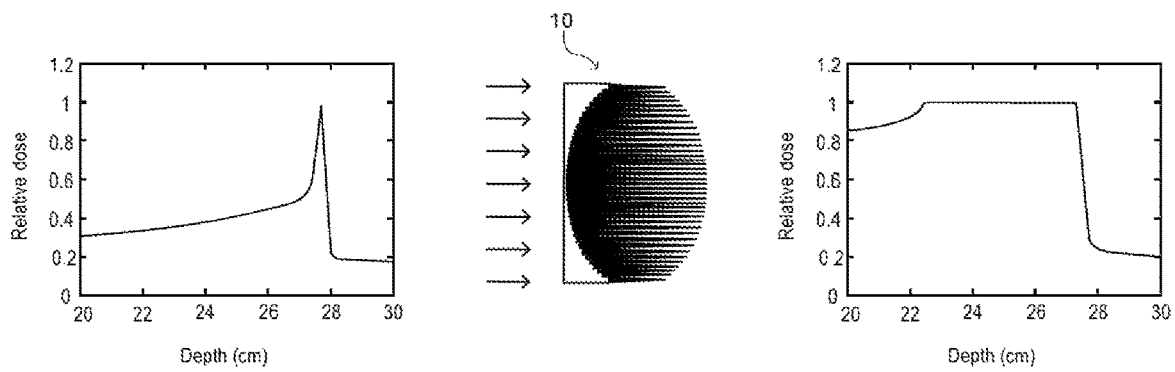
FIG. 2b illustrates the dose depth of the incoming beam upstream of the device and the resulting depth dose distribution in the patient.

FIG. 2b corresponds to the situation of FIG. 2a. The diagram on the left depicts the depth dose of the incoming beam upstream of the device. As can be seen, most of the dose would be deposited at one particular depth, corresponding to the energy of the protons in the beam. The diagram on the right depicts the depth dose after the beam passes through the modulation device 10. As can be seen, the depth dose has a broader range, corresponding to dose deposition throughout the target 27. Although FIGS. 2a and 2b show the modulation device 10 inserted in the beam with the protrusions 13 downstream of the disk 11, it could also be placed in the opposite direction, that is with the protrusions upstream of the disk.

Figure 3:
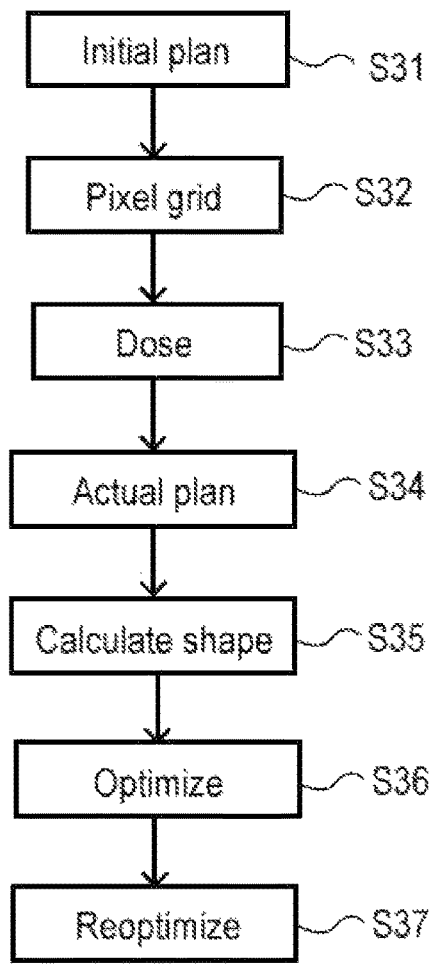
FIG. 3 is a flow chart of a method according to an embodiment of the invention

FIG. 3 is a flow chart of a method according to an embodiment of the invention for designing a compensation element. While the method is described here for protons, it can be applied to any type of ion used in radiotherapy.

In step S31, a conventional treatment plan, typically a pencil beam scanning plan, is obtained. The plan may be obtained in any suitable way known in the art. Typically this is done by optimization based on an optimization problem comprising objective functions and/or constraints reflecting the desired properties, and results in a dose distribution and an optimized treatment plan. This means that, assuming a virtual pixel grid in a cross-section of the beam upstream of the patient, the energy spectrum and optionally the proton direction distribution for each pixel in the cross-section of the beam upstream of the patient will be known. Characteristics of a radiation beam to be used for dose delivery to the patient are also determined. The radiation beam may be homogeneous or inhomogeneous but in the simplest case is a homogeneous beam in which all ions have the same energy initially.

In step S32, optionally the pixel grid is projected outside of the patient in a plane, the pixels in the pixel grid corresponding to the pixels in the cross-section mentioned for step S31. The position of the pixel grid preferably corresponds to the position the compensation element will be placed in during treatment. The distance to the patient may be selected freely; in some implementations 5 centimeters have been found to be a suitable distance.

The size of each pixel may be, for example, 1.5 mm×1.5 mm. The energy spectrum at each pixel is a direct function of the plan, given a specific sequence of incoming energy levels of the field.

In step S33 the dose is recalculated using a dose engine, for example a Monte Carlo dose engine. During the recalculation certain quantities are scored for each pixel in the pixel grid, to be used in designing the compensation element. For example, the proton energies in each pixel in the pixel grid may be accumulated in an energy spectrum per pixel. The quantities that are scored may, for example, include one or more of the following:
Energy layer index spectrum per pixel.
Water equivalent depth spectrum at proton trackends.
Proton energy Based on the scored data for each pixel of the pixel grid, in step S34 it is determined how the radiation beam to be used for dose delivery should be affected in the area corresponding to each pixel. For each pixel, the ions having passed through the element should ideally have the same energy spectrum as calculated in step S33. Based on the spectrum, a protrusion shape can be calculated for each pixel in step S35, that will yield an energy spectrum per pixel in the dose delivery beam that is sufficiently similar to the energy spectrum calculated in step S33 to ensure sufficient quality in the dose delivery. The same procedure can be applied for the other choices of scored data. The calculation of the protrusion shape may also include the selection of an appropriate material for the protrusion, that is, one that, together with the shape, will affect the ions passing through that pixel in the desired way.

The protrusion designed for each pixel does not have to be shaped as a pin or have any type of symmetry, although a circular symmetry may be easier to achieve than a more complex shape. It can instead be any type of elongate body, or set of elongate bodies, extending from the compensator element in the direction of the beam. It could be composed of a number of different protrusions, such as spikes, pins or elongate sheets, within one pixel. The lengths of different fractions of the elongate body or bodies extending in one pixel are selected in such a way that the ions passing through that pixel will be affected differently to result in an energy spectrum of the ions corresponding to the energy spectrum calculated in step S33. As mentioned above, the dose delivery beam may be homogeneous, but the method is also applicable to a more complex dose delivery beam, as long as its properties are known.

The resulting shape data for each elongate body or set of bodies may be used for triangulation to generate a Computer-Aided Design (CAD) file that may be used for producing the compensating device, for example, by three-dimensional (3D) printing. Alternatively, some additional optimization steps may be performed in step S36, to improve the resulting compensating device before it is produced, i.a. by taking into account possible scattering from the elongate bodies.

One or more further additional optimization step S37 may include, after determining the geometry of the compensating device per beam, performing a final Pencil Beam Scanning (PBS) re-optimization taking the geometry of the compensating device into account in the re-optimization. This will help fine tune the plan further. The final optimization is performed with a single energy layer per plan. The final optimization can include multiple beams and any type of advanced objective function such as functions related to RBE dose, LET or robustness.

Alternatively, the additional optimization of step S37 can be done with multiple energy layers. If the design and effect of the compensation device are perfect, the optimized plan should place all weights in a single energy layer. If the layer weight spread is above some limit this data can be used to adjust the geometry of the compensating device. This procedure can be iterated until the hedgehog geometry is stable between iterations. A similar approach should be possible to apply to optimization of standard compensators for passive planning.

The use of a pixel grid, as foreseen in step S32, is not necessary but is advantageous for simplifying the procedure. It should be noted that the shape of the pixels may be selected as suitable. The pixels may be square or hexagonal or have any other feasible shape.

As mentioned above, the resulting compensation device may be used to shape and modulate the field for any type of ion-based radiation treatment. In particular, it will enable a reduction in the number of energy layers used, making the delivery of the treatment faster. Preferably, delivery using only one energy layer is enabled by designing the elongate bodies so that they ensure coverage of the whole, three-dimensional target from one field.

Figure 4:
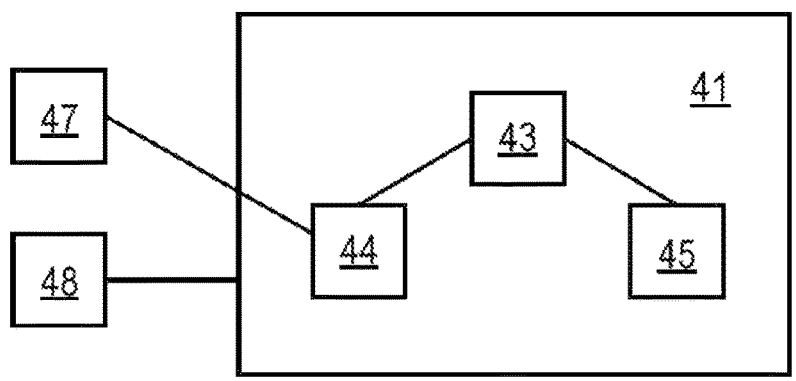
FIG. 4 is a schematic drawing of a computer system in which the inventive method may be carried out.

FIG. 4 is a schematic overview of a computer system in which the optimization according to the invention may be carried out. A computer 41 comprises a processor 43, a data memory 44 and a program memory 45. Preferably, a user input means 47, 48 is also present, in the form of a keyboard, a mouse, a joystick, voice recognition means or any other available user input means. The user input means may also be arranged to receive data from an external memory unit.

An optimized PBS treatment plan is found in the data memory 44. The treatment plan may be generated in the computer 41, or received from another storage means in any way known in the art. The data memory also comprises the characteristics of the dose delivery beam to be used in the actual treatment of the patient, that is, the beam that is to be modulated by the compensation device.

The data memory 44 also holds properties of the modulating device such a its material composition. If the material is known, its properties may be stored. If the process includes selecting one of a number of available materials to be used, the properties of all available materials should be stored, including their mass densities and manufacturing limitations. As will be understood, the data memory 44 is only shown schematically. There may be several data memory units, each holding one or more different types of data, for example, one data memory for the design of the compensation device, etc.

The program memory 45 holds a computer program arranged to control the processor to perform the design procedure according to the invention. The program memory may also hold instructions for how to convert the design of the compensation device to instructions to a manufacturing machine, for example, a 3D printer arranged to produce the compensation device.

The invention claimed is:

1. A method of designing a compensating device for use in ion-based radiotherapy treatment delivery, the device including a substantially disk-shaped structure including on one side of the disk a plurality of elongate elements, the method comprising the steps of:

a. obtaining a pencil beam scanning initial treatment plan, wherein the initial treatment plan is optimized with respect to one or more of: Physical dose, Relative Biological Effective dose, and Linear Energy Transfer objectives;

b. obtaining characteristics of an actual treatment plan, the actual treatment plan comprising at least one beam to be used for treating the patient;

c. determining at least one parameter, the parameter being characteristic of the desired energy modulation of the actual treatment plan, by performing a dose calculation of the initial treatment plan;

d. based on the at least one parameter, computing a shape for each of the plurality of elongate elements to modulate the dose of the delivery beam to mimic the dose of the initial treatment plan per beam;

e. re-optimizing the actual treatment plan, wherein the re-optimization uses a single energy layer and takes into account the compensating device, to produce a final treatment plan to be used in delivery to the patient;

f. adjusting the shape of one or more of the elongate elements, based on the results of the re-optimizing; and g. iterating steps e and f until the final treatment plan and the geometry of the compensating device remain stable between successive iterations.

2. A method according to claim 1, wherein the dose of the actual treatment plan is calculated and the quantities scored for pixels placed on a virtual grid projected upstream of the patient in the beam trajectory of the at least one beam.

3. A method according to claim 1, wherein the step of computing a shape also includes selecting a material for the elongate body or bodies.

4. A method according to claim 1, wherein the at least one parameter includes energy layer index spectrum of the initial treatment plan, for determining the shape of the elongate bodies.

5. A method according to claim 1, wherein the at least one parameter includes the energy spectrum of the initial treatment plan for determining the height of the elongate bodies.

6. A method according to claim 1, wherein the at least one parameter includes water equivalent depth spectrum at the primary proton trackends of the initial treatment plan, for determining the height of the elongate bodies.

7. A method according to claim 1, wherein the actual treatment plan includes a homogeneous radiation field.

8. A method according to claim 1, wherein the actual treatment plan is used as a final treatment plan.

9. A method according to claim 1, comprising the step of obtaining element shape data indicating the shape of each elongate element, based on the actual treatment plan and using the element shape data to generate a file comprising instructions for the design of the compensating device.

10. A method according to claim 1, wherein the final treatment plan is a pencil beam scanning plan or a double scattering plan or a single scattering plan or a wobbling plan.

11. A method of manufacturing a compensating device for use in ion-based radiotherapy treatment delivery, comprising performing the method according to claim 1, using the shape data resulting from the plan to generate a file comprising instructions for the design of the compensating device.

12. A computer program product comprising a non-transitory computer-readable storage medium having program instructions embodied therewith which, when run in a computer will cause the computer to perform the method according to claim 1.

13. A computer system comprising a program memory and a processor arranged to execute a program found in the program memory, the program memory comprising a computer program product according to claim 12.

* * * * *